(12) United States Patent
Golz-Berner et al.

(10) Patent No.: US 6,843,995 B2
(45) Date of Patent: Jan. 18, 2005

(54) COSMETIC PREPARATION CONTAINING EXTRACTS OF TUBERACEAE

(75) Inventors: Karin Golz-Berner, Monaco (DE); Leonhard Zastrow, Monaco (DE)

(73) Assignee: Coty B.V. (NL)

( * ) Notice: Subject to any disclaimer, the term of this patent is extended or adjusted under 35 U.S.C. 154(b) by 0 days.

(21) Appl. No.: 10/398,963

(22) PCT Filed: Oct. 5, 2001

(86) PCT No.: PCT/DE01/03871

§ 371 (c)(1),
(2), (4) Date: Apr. 11, 2003

(87) PCT Pub. No.: WO02/30384

PCT Pub. Date: Apr. 18, 2002

(65) Prior Publication Data

US 2004/0009143 A1 Jan. 15, 2004

(30) Foreign Application Priority Data

Oct. 13, 2000 (DE) .......................... 10053051

(51) Int. Cl.$^7$ .......................... A61K 35/84; A61K 7/00; A61K 7/26

(52) U.S. Cl. .................. 424/195.15; 424/401; 424/488; 424/493

(58) Field of Search .............................. 424/195.5, 401, 424/488, 493

(56) References Cited

FOREIGN PATENT DOCUMENTS

JP 06040933 * 2/1994

* cited by examiner

*Primary Examiner*—Patricia Leith
(74) *Attorney, Agent, or Firm*—Pendorf & Cutliff

(57) ABSTRACT

The invention relates to a cosmetic preparation containing an active complex comprised of extracts. The active complex contains at least one starting substance, which is extracted as an aqueous extract from real truffles (Tuberaceae) and which is provided in a cosmetically acceptable gel while being stabilized. A preferred active complex is one that additionally contains a champagne product. Cosmetic preparations containing this active complex lead to an improved stimulation of the immune system, an improved regenerative effect and thus to an improved balance in the ecosystem of the skin.

9 Claims, No Drawings

COSMETIC PREPARATION CONTAINING EXTRACTS OF TUBERACEAE

BACKGROUND OF THE INVENTION

Field of the Invention

The invention relates to a cosmetic preparation containing an active complex comprised of plant extracts.

A large number of cosmetic products have already been described which comprise plants or parts of plants that are integrated into the aforesaid products directly or in the form of extracts. These plants include e.g. algae, various herbs known as medicinal plants, cereals, extracts from tea, coffee and fruit, bark extracts and yeast extracts, etc. The plants are used with the aim of utilizing their active agents for cosmetic purposes, particularly with the aim of enabling the aforesaid agents to become effective in the upper layers of the skin. Hardly any fungal extracts other than the aforesaid yeast extracts have been used for this purpose to date, mainly because nearly no substances having an effect on the skin have become known in this area.

SUMMARY OF THE INVENTION

The object of the invention is to make further plant-based active agents available for cosmetic purposes, in particular to combine different active agents stemming from different plants into new active complexes.

DETAILED DESCRIPTION OF THE INVENTION

According to the invention, a cosmetic preparation containing plant extracts is provided, which preparation contains an active complex comprised of at least one starting substance extracted as an aqueous extract from common truffles (Tuberaceae) and is provided in a cosmetically acceptable gel while being stabilized.

Common truffles include e.g. Burgundy truffles (*Tuber uncinatum*), Perigord truffles (*Tuber melanosporum* Vitt.), Kalahari truffles (*Terfezia pfeilii* Hennings), Piedmont truffles (*Tuber magnatum Pico Vitt.*), lion's truffles (*Terfezia leonis* Tul.), summer truffles (*Tuber aestivum*), winter truffles (*Tuber brumale* Vitt.) and white truffles (*Choiromyces maeandriformis*). Particularly preferred are truffle species are *Tuber uncinatum, Tuber melanosporum* Vitt., *Tuber magnatum* Pico Vitt., *Tuber aestivum, Choiromyces maeandri*-formis, *Tuber brumale* Vitt. and mixtures thereof, particularly *Tuber melanosporum* Vitt.

Common truffles, which belong to the class of ascomycetes, order of Tuberales, have been appreciated as excellent edible fungi for many centuries and are of outstanding importance due to their special aroma. Truffles are underground fungi growing in symbiosis with oak tree roots and forming tuber-like fruiting bodies.

In the extraction process from truffles, several active agents are set free. It has been found that a non-specific stimulation of the immune system can be achieved and the body's antiviral defence mechanisms improved thanks to the aqueous truffle extracts' contents of essential amino acids, vitamins B1, B2 and B3, polysaccharides such as letinan and eritadenin, and the stabilization of the aforesaid active agents in a cosmetic product. With regard to the skin, this brings about an excellent regenerative effect and in addition an effect against hair loss.

A special active complex is prepared by incorporating champagne products, e.g. a champagne whose liquid components have been removed, e.g. by means of spray-drying. Based on the special bottle fermentation of French wines from Champagne, a sparkling wine is obtained which has a high content of polysaccharides, in addition to flavonoids, pro-cyanidolic oligomers (P.C.O.) and tannins. The incorporation of the aforesaid champagne product into the active complex containing truffle extract leads to a clearly improved balance in the ecosystem of the skin, thus strengthening the skin's natural protective barrier and stimulating the activity of the mediators present, i.e. leucotrienes, prostaglandins, interleukins and other cytokinins, particularly in situations which stress the skin.

In addition, the active complex has a toning and an energizing effect as well as a stabilizing and a softening effect and at the same time counteracts irritations.

The active complex is provided in a gel while being stabilized. The stabilization can be achieved e.g. by means of a phospholipid in which the pulverized basic components of the active complex, i.e. Tuberaceae extract and, if desired, champagne product, are dispersed and which is then distributed in a gel in a homogeneous manner. Due to the aforesaid homogeneous distribution in a gel, a form of the active complex is obtained which on the one hand is a stable, liquid form of the active agents and an excellent basis for further processing into various cosmetic products on the other.

Phospholipids which can be used include e.g. Phosphatidylcholine, Phosphatidylethanolamine, Phosphatidylinositol, Phosphatidylserine, Phosphatidic Acid and lysolecithins as well as mixtures thereof. Known products are e.g. Phoslipon® or NAT®.

The active complex can be contained in the cosmetic preparation in an amount ranging from 0.05 to 25% by weight, the amounts of Tuberaceae extract and, if desired, champagne product jointly making up 1 to 15% by weight of the active complex.

There are no restrictions as regards the ratio in which Tuberaceae extract and the champagne product are contained in the active complex. It is preferred that the ratio be in the range from 25:75 to 75:25 relative to the agents' dry mass.

Gel-forming agents which can be used as gels include e.g. Carbomer, Xanthan Gum, Carrageenan, Acacia Gum, Guar Gum, Agar-Agar, alginates and tylosen, carboxymethyl cellulose, hydroxyethyl cellulose, certain polyacrylates, polyvinyl alcohol, polyvinylpyrrolidone, montmorillonite. Particularly preferred substances are Carbomer, Xanthan Gum, Carrageenan, Acacia Gum, Guar Gum, Agar-Agar, alginates, carboxymethyl cellulose, hydroxyethyl cellulose and mixtures thereof.

The preparation according to the invention further contains cosmetic auxiliaries and carrier substances as they are commonly used in such preparations, e.g. water, preservatives, vitamins, colourants, pigments having a colouring effect, scavengers, thickeners, emollients, moisturizing substances, fragrances, alcohols, polyols, esters, shellac, electrolytes, polar and non-polar oils, polymers, copolymers, emulsifiers, waxes, stabilizers.

Further additives or active agents contained in the cosmetic compositions can be vitamins such as Vitamin A or derivatives thereof, coloured plant extracts, â-carotene, organic water-soluble or oil-soluble sunscreens such as e.g. Octyl Methoxycinnamate; inorganic sunscreens such as $TiO_2$, $ZnO$, $SiO_2$.

Advantageously, a further active agent contained in the preparation can be Kaolin according to WO96/17588, which Kaolin has been modified with spherical $TiO_2$ or $SiO_2$ particles the particle size of which is <5 im, the aforesaid spherical particles making up 0.5 to 10% by weight of the kaolin mixture. In this way, the preparation feels very soft on the skin and has an additional anti-inflammatory effect. The modified Kaolin can be contained in the range of 0.1–6% by weight relative to the total weight of the preparation.

Further cosmetic active agents include e.g. emulsifiers, scavengers, moisturizing substances, enzymes, further plant-based active agents, polymers, melanin, antioxidants, anti-inflammatory natural active agents, asymmetric lamellar aggregates loaded with oxygen according to WO94/00109 or decomposition products of yeasts, algae or other vegetable substances produced by means of a gentle ultrasonic decomposition process according to WO94/13783.

Cosmetic preparations containing the active complex according to the invention can be provided as an O/W emulsion, a W/O emulsion or a gel.

Suitable emulsifiers for O/W emulsions include e.g. addition products of 2–30 moles ethylene oxide to linear $C_8$–$C_{22}$ fatty alcohols, to $C_{12}$–$C_{22}$ fatty acids and to $C_8$–$C_{15}$ alkyl phenols; $C_{12}$–$C_{22}$ fatty acid monoesters and diesters of addition products of 1–30 moles ethylene oxide to glycerine.

Suitable emulsifiers for W/O emulsions include e.g. addition products of 2–15 moles ethylene oxide to castor oil; esters of $C_{12}$–$C_{22}$ fatty acids and glycerine, polyglycerine, pentaerythrite, sugar alcohols (e.g. sorbitol), polyglucosides (e.g. cellulose); polyalkylene glycols; wool wax alcohols; copolymers of polysiloxane polyalkylpolyether.

Oils and fats which are suitable for forming the oil phase of an O/W emulsion or a W/O emulsion according to the invention include e.g. mineral oils, fatty acid triglycerides, silicone oils as well as vegetable oils such as Calendula Oil, Jojaba Oil, Avocado Oil, Macadamia Nut Oil, Castor Oil, Wheat Germ Oil, Babassu Oil, Grapeseed Oil, Kukui Nut Oil, Thistle Oil, Evening Primrose Oil, Safflower Oil or a mixture of several thereof.

In addition, esters or ethers can be used, such as e.g. Dipentaerythrityl Hexacaprilate/Hexacaprate/Tridecyl Trimellitate/Tridecyl Stearate/Neopentyl Glycol Dicaprylate Dicaprate, Propylene Glycol Dioctanoate 5, Propylene Glycol Dicaprylate 2,30 Dicaprate, Tridecyl Stearate/Neopentyl Glycol Dicaprylate Dicaprate/Tridecyl Trimellitate, Neopentyl Glycol Dioctanoate, Isopropyl Myristate, Diisopropyl Dimer Dilinoleate, Trimethylpropane Triisostearate, Myristyl Ether, Stearyl Ether, Butyl Ether, Dicaprylyl Ether, PPG1-PEG9 Lauroyl Glycol Ether, PPG15 Stearyl Ether, PPG14 Butyl Ether, Fomblin HC25.

Further emollients used can include compounds such as Stearyl alcohol, Glyceryl monoricinoleate, Glyceryl monostearate, Propane-1,2-diol, Butane-1,3-diol, Cetyl Alcohol, Isopropyl Isostearate, Stearic Acid, Isobutyl Palmitate, Oleyl Alcohol, Isopropyl Laurate, Decyl Oleate, Octadecane-2-ol, Isocetyl Alcohol, Cetyl Palmitate, silicone oils such as Dimethyl Polysiloxane, Isopropyl Myristate, Isopropyl Palmitate, Polyethylene Glycol, Lanolin, Cocoa Butter, vegetable oils such as Maize Oil, Cotton seed Oil, Olive Oil, mineral oils, Butyl Myristate, Palmitic Acid, etc.

The cosmetic preparation according to the invention can be used e.g. in sun creams, sun gels, after-sun products, day creams, night creams, moisturizing creams, masks, body lotions, cleansing milk, make-ups, lipsticks, mascara, care sticks, body powder, eye cosmetics, hair masks, hair conditioners, hair shampoos, hair lotions, shower gels, soaps, compact powders. The aforesaid products are manufactured in a way known to those skilled in the art.

According to the invention, the method for manufacturing a cosmetic preparation containing plant extracts comprises the steps of a) mixing pieces of Tuberaceae with water during a period of between 1.5 and 12 hours, b) leaving the mixture to soak for 0.5 to 12 hours, c) separating the aqueous phase, removing its liquid components and sterilizing it, d) dispersing the sterilized powder in an aqueous phospholipid at at least 10,000 to approx. 15,000 rpm, e) distributing the dispersion in a cosmetically acceptable gel in a homogeneous manner and neutralizing it, f) bringing the gel into contact with further cosmetic auxiliaries, carrier substances or active agents or mixtures thereof and formulating a cosmetic preparation.

The extract can be separated by means of filtration and at the same time decolourized, if necessary, e.g. using activated carbon.

The invention will hereinafter be explained in more detail by means of examples. All amounts are given in % by weight if not indicated otherwise.

EXAMPLES 1 TO 4

Preparation of the Active Complex a) 1 kg Perigord truffles (*Tuber melanosporum* Vitt.) are cut into pieces and mixed with 5 l water at at least 1,000 rpm for 5 hours. The mixture is left to soak over night and subsequently filtered. The clear filtrate is applied onto a spray-drier and the powder obtained subsequently sterilized.

b) 10 bottles of white champagne are spray-dried. The white powder obtained is subsequently sterilized.

In order to prepare the active complex, the truffle extract and, if desired, the same amount of champagne extract is/are added into water, the mixture is combined with an aqueous phospholipid (NAT80®) and stirred at at least 10,000 rpm at room temperature to form a dispersion. Subsequently, the dispersion is brought into contact with the aqueous gel, stirred and neutralized. Glycerine and ethanol can be stirred in as additional substances in order to improve the mixture's processability. A stabilized active complex having very good storing properties is obtained.

| Components of the active complex | Ex. 1 | Ex. 2 | Ex. 3 | Ex. 4 |
|---|---|---|---|---|
| Water, dist. | ad 100 | ad 100 | ad 100 | ad 100 |
| Carbomer | 0.5 | 0.5 | 0.5 | 0.2 |
| Glycerine | 6.0 | 6.0 | 6.0 | — |
| Preservative | 0.9 | 0.9 | 0.9 | 1.0 |
| Triethanolamine | 0.5 | 0.5 | 0.5 | 0.5 |
| Ethanol | 6.0 | 3.0 | 1.0 | — |
| *Tuber melanosporum* Vitt. (dry extract) | 2.0 | 3.8 | 3.5 | — |
| *Tuber aestivum* (dry extract) | — | — | — | 4.0 |
| Champagne product (spray-dried) | 2.0 | 5.0 | 1.5 | — |
| Phospholipid | 8.0 | 8.0 | 8.0 | 5.0 |

EXAMPLE 1a

The same composition as in Example 1 is used, except that it contains 6% by weight of the dry extract from *Tuber melanosporum* Vitt. and 5% by weight of the dried champagne product.

EXAMPLE 4a

The same composition as in Example 4 is used, except that it contains 8% by weight of the dry extract from *Tuber aestivum* and 5% by weight of a dried champagne product is used.

EXAMPLE 5

Cream I

| Phase A | |
|---|---|
| Water | ad 100 |
| Glycerine | 5.0 |
| Crosspolymers | 0.2 |
| Phase B | |
| Cetearyl Alcohol | 1.5 |
| Isohexadecane | 3.5 |
| Octyl Stearate | 3.0 |
| Phase C | |
| Triethanolamine (TEA) | 0.2 |
| Phase D | |
| Active complex according to Example 1 | 2.0 |
| Preservative | 0.5 |
| Perfume oil | 0.3 |

Phase A and Phase B are heated separately up to 65° C. while stirring and combined with each other while stirring. The temperature is reduced to approx. 50° C. and Phase C added. Phase D is stirred in at approx. 35° C.

EXAMPLE 6

Cream II

| Phase A | |
|---|---|
| Water | ad 100 |
| Polyacrylamide | 1.5 |
| C13–14 Isoparaffin | 2.0 |
| Laureth 7 | 2.0 |
| Phase B | |
| Babassu Oil | 2.5 |
| Sesame Oil | 7.0 |
| Kaolin according to WO96/17588, Ex. 1 | 5.0 |
| Phase C | |
| Active complex according to Example 2 | 5.0 |
| Perfume oil | 0.5 |

Phase A and Phase B are prepared separately and then combined with each other at 40° C. while stirring. Once the mixture had been cooled down to approx. 35° C., Phase C was stirred in.

EXAMPLE 7

Sun Cream

| Phase A | |
|---|---|
| Water | ad 100 |
| Propylene Glycol | 3.0 |
| PVM/MA Decadiene Crosspolymer | 0.5 |
| Benzophenone-3 | 2.5 |
| Phase B | |
| Octyl Stearate | 5.0 |
| Isohexadecane | 3.5 |
| Dimethicone | 1.0 |
| Phase C | |
| Pongamina extract (*Pongamina pinnata*) | 1.0 |
| Shellac | 1.0 |

-continued

| Octyl Methoxycinnamate | 7.5 |
|---|---|
| Butyl Methoxydibenzoylmethane | 2.0 |
| Phase D | |
| Active complex according to Example 3 | 8.0 |
| Aloe vera | 0.5 |
| Preservative | 0.5 |
| Perfume oil | 0.5 |

Phase A and Phase B are heated separately up to 65° C. and combined with each other while stirring. The temperature is reduced to approx. 60° C. and Phase C is added. Phase D is stirred in at approx. 35° C.

EXAMPLE 8

Cream III

| Phase A | |
|---|---|
| Water | ad 100 |
| Glycerine | 5.5 |
| Crosspolymer | 0.2 |
| Phase B | |
| Cetearyl Alcohol | 1.8 |
| Isohexadecane | 3.2 |
| Octyl Stearate | 3.0 |
| Phase C | |
| TEA | 0.2 |
| Phase D | |
| Active complex according to Example 4 | 10.0 |
| Preservative | 0.5 |
| Perfume oil | 0.3 |

EXAMPLE 9

A cream is prepared according to Example 5 containing an active complex according to Example 1a which makes up 10% of the whole composition.

EXAMPLE 10

A sun cream is prepared according to Example 7 containing an active complex according to Example 4a which makes up 12% of the whole composition.

What is claimed is:

1. A cosmetic preparation comprising an active complex which is comprised of at least one aqueous extract of common truffles (Tuberacea) together with spray-dried champagne, wherein the active complex is provided in a cosmetic acceptable gel and stabilizer and wherein said cosmetic preparation is manufactured by the following steps:

a) mixing pieces of Tuberacea with water for a period of between 1.5 and 12 hours,
   b) leaving the mixture to soak for 0.5 to 12 hours to create an aqueous and a solid phase,
   c) separating the aqueous phase from the solid phase, and sterilizing the aqueous phase to form a powder of the sterilized aqueous phase,
   d) dispersing the sterilized powder and a spray-dried champagne in an aqueous phospholipid at at least 10,000 rpm,
   e) distributing the dispersion of part (d) into a cosmetically acceptable gel in a homogeneous manner and neutralizing, and f) mixing the gel of part (e) with further cosmetic auxiliaries, carrier substances, active agents or mixtures thereof to formulate a cosmetic preparation.

2. A preparation according to claim 1 wherein the Tuberaceae are selected from among *Tuber uncinatum, Tuber melanosporm Vitt., Tuber magnatum Pico Vitt.*, Tuber aestivum, *Choiromyces maeandriformis, Tuber brumale Vitt.* and mixtures thereof.

3. A preparation according to claim 1 wherein the Tuberaceae extract and the champagne product are present in the active complex in a ratio ranging from 25:75 to 75:25 of the dry weight of active complex.

4. A preparation according to claim 1 wherein the stabilizer comprises a phospholipid.

5. A preparation according to claim 1 wherein the gel is selected from Carbomer, Xanthan Gum, Carrageenan, Acacia Gum, Guar Gum, Agar-Agar, alginates, carboxymethyl cellulose, hydroxyethyl cellulose and mixtures thereof.

6. A preparation according to claim 1 wherein the active complex in addition contains at least one protective agent against UV radiation.

7. A preparation according to claim 6 wherein the said preparation is provided in the form of a cream selected from day creams, night creams, sun creams, body lotions, make-up, eye cosmetics special eye cream, eyeshadow, hair shampoos and shower gels.

8. The preparation according to claim 1 wherein the active complex is present in an amount ranging from 0.05 to 25% by weight of the preparation an the amounts of Tuberaceae extract and spray-dried champagne are present together from 1 to 15% by weight of the active complex.

9. A method for manufacturing a cosmetic preparation comprising the steps of:
   a) mixing pieces of Tuberacea with water for a period of between 1.5 an 12 hours,
   b) leaving the mixture to soak for 0.5 to 12 hours to create an aqueous and a solid phase,
   c) separating the aqueous phase from the solid phase, and sterilizing the aqueous phase to form a powder of the sterilized aqueous phase,
   d) dispersing the sterilized powder and a spray-dried champagne in an aqueous phospholipid at at least 10,000 rpm,
   e) distributing the dispersion of part (d) into a cosmetically acceptable gel in a homogeneous manner and neutralizing, and
   f) mixing the gel of part (e) with further cosmetic auxiliaries, carrier substances, active agents or mixtures thereof to formulate a cosmetic preparation.

* * * * *